(12) United States Patent
Abdou

(10) Patent No.: US 8,870,920 B2
(45) Date of Patent: Oct. 28, 2014

(54) DEVICES AND METHODS FOR INTER-VERTEBRAL ORTHOPEDIC DEVICE PLACEMENT

(76) Inventor: M. Samy Abdou, San Diego, CA (US)

( * ) Notice: Subject to any disclaimer, the term of this patent is extended or adjusted under 35 U.S.C. 154(b) by 1890 days.

(21) Appl. No.: 11/544,452

(22) Filed: Oct. 6, 2006

(65) Prior Publication Data

US 2007/0093828 A1   Apr. 26, 2007

Related U.S. Application Data

(63) Continuation-in-part of application No. 11/286,152, filed on Nov. 23, 2005, now Pat. No. 8,172,855.

(60) Provisional application No. 60/724,632, filed on Oct. 7, 2005.

(51) Int. Cl.
| | |
|---|---|
| *A61B 17/70* | (2006.01) |
| *A61B 17/02* | (2006.01) |
| *A61B 17/34* | (2006.01) |
| *A61B 17/90* | (2006.01) |
| *A61F 2/46* | (2006.01) |

(52) U.S. Cl.
CPC ....... *A61B 17/025* (2013.01); *A61B 2017/0256* (2013.01); *A61B 17/3468* (2013.01); *A61B 2017/90* (2013.01); *A61F 2/4611* (2013.01); *A61B 17/7077* (2013.01)
USPC ........................................................ 606/248

(58) Field of Classification Search
USPC .................... 606/86 A, 90, 97, 246–249, 279
See application file for complete search history.

(56) References Cited

U.S. PATENT DOCUMENTS

| | | | |
|---|---|---|---|
| 2,248,054 | A | 7/1941 | Becker |
| 3,090,386 | A | 5/1963 | Babcock |
| 3,659,595 | A | 5/1972 | Haboush |
| 4,037,592 | A | 7/1977 | Kronner |
| 4,569,662 | A | 2/1986 | Dragan |
| 4,580,563 | A | 4/1986 | Gross |
| 4,722,331 | A | 2/1988 | Fox |
| 4,790,303 | A | 12/1988 | Steffee |
| 4,899,761 | A | 2/1990 | Brown et al. |

(Continued)

FOREIGN PATENT DOCUMENTS

| | | |
|---|---|---|
| DE | 10035182 | 2/2002 |
| EP | 77159 | 4/1983 |

(Continued)

OTHER PUBLICATIONS

U.S. Appl. No. 11/286,152, filed Nov. 23, 2005.

(Continued)

*Primary Examiner* — Matthew Lawson
(74) *Attorney, Agent, or Firm* — Gazdzinski & Associates, PC

(57) ABSTRACT

Disclosed are devices and methods for the controlled movement of neighboring vertebrae and the delivery of an orthopedic implant between adjacent spinous processes. The methods are especially adapted to be performed using minimally invasive surgery or in a percutaneous manner. An exemplary method comprises advancing a first segment of a threaded first distraction screw into a bony surface of a spinous process of the first vertebral bone, coupling a first segment of a second distraction screw onto a segment of a second vertebral bone, positioning an orthopedic implant at a desired target site, and removing one of the first and second distraction screws.

17 Claims, 17 Drawing Sheets

(56) References Cited

U.S. PATENT DOCUMENTS

| | | |
|---|---|---|
| 4,903,692 A | 2/1990 | Reese |
| 5,254,118 A | 10/1993 | Mirkovic |
| 5,275,601 A | 1/1994 | Goglewski et al. |
| 5,330,468 A | 7/1994 | Burkhart |
| 5,334,205 A | 8/1994 | Cain |
| 5,354,292 A | 10/1994 | Braeuer et al. |
| 5,360,429 A | 11/1994 | Jeanson et al. |
| 5,484,440 A | 1/1996 | Allard |
| 5,531,747 A | 7/1996 | Ray |
| 5,545,164 A | 8/1996 | Howland |
| 5,558,674 A | 9/1996 | Heggeness et al. |
| 5,569,248 A | 10/1996 | Mathews |
| 5,609,634 A | 3/1997 | Voydeville |
| 5,616,142 A | 4/1997 | Yuan et al. |
| 5,672,176 A | 9/1997 | Biedermann et al. |
| 5,681,312 A | 10/1997 | Yuan et al. |
| 5,928,139 A | 7/1999 | Koros et al. |
| 5,971,987 A | 10/1999 | Huxel et al. |
| 5,976,146 A | 11/1999 | Ogawa et al. |
| 5,993,449 A | 11/1999 | Schlapfer et al. |
| 6,039,761 A | 3/2000 | Li et al. |
| 6,059,786 A | 5/2000 | Jackson |
| 6,086,589 A | 7/2000 | Kuslich |
| 6,090,113 A | 7/2000 | Le Couedic et al. |
| 6,117,135 A | 9/2000 | Schlapfer et al. |
| 6,123,707 A | 9/2000 | Wagner |
| 6,139,549 A | 10/2000 | Keller |
| 6,159,244 A | 12/2000 | Suddaby |
| 6,193,757 B1 | 2/2001 | Foley et al. |
| 6,306,136 B1 | 10/2001 | Baccelli |
| 6,309,391 B1 | 10/2001 | Crandell et al. |
| 6,319,002 B1 | 11/2001 | Pond |
| 6,319,257 B1 | 11/2001 | Carignan et al. |
| 6,331,179 B1 | 12/2001 | Freid et al. |
| 6,332,882 B1 | 12/2001 | Zucherman et al. |
| 6,355,038 B1 | 3/2002 | Pisharodi |
| 6,402,752 B2 | 6/2002 | Schaffler-Wachter et al. |
| 6,419,676 B1 | 7/2002 | Zucherman et al. |
| 6,428,576 B1 | 8/2002 | Haldimann |
| 6,432,140 B1 | 8/2002 | Lin |
| 6,440,133 B1 | 8/2002 | Beale et al. |
| 6,451,019 B1 | 9/2002 | Zucherman et al. |
| 6,451,020 B1 | 9/2002 | Zucherman et al. |
| 6,478,800 B1 | 11/2002 | Fraser et al. |
| 6,508,839 B1 | 1/2003 | Lambrecht et al. |
| 6,514,256 B2 | 2/2003 | Zucherman et al. |
| 6,530,929 B1 | 3/2003 | Justis et al. |
| 6,558,386 B1 | 5/2003 | Cragg |
| 6,558,390 B2 | 5/2003 | Cragg |
| 6,599,290 B2 | 7/2003 | Bailey |
| 6,599,294 B2 * | 7/2003 | Fuss et al. .......... 606/99 |
| 6,599,295 B1 | 7/2003 | Tornier et al. |
| 6,645,207 B2 | 11/2003 | Dixon et al. |
| 6,663,631 B2 | 12/2003 | Kuntz et al. |
| 6,695,842 B2 | 2/2004 | Zucherman et al. |
| 6,699,246 B2 | 3/2004 | Zucherman et al. |
| 6,716,212 B1 | 4/2004 | Pickens |
| 6,730,126 B2 | 5/2004 | Boehm, Jr. et al. |
| 6,733,534 B2 * | 5/2004 | Sherman .................. 623/17.16 |
| 6,739,068 B1 | 5/2004 | Rinner |
| 6,740,087 B2 * | 5/2004 | Knox .......... 606/86 A |
| 6,740,090 B1 | 5/2004 | Cragg et al. |
| 6,746,449 B2 | 6/2004 | Jones et al. |
| 6,749,614 B2 | 6/2004 | Teitelbaum et al. |
| 6,755,841 B2 | 6/2004 | Fraser et al. |
| 6,761,720 B1 | 7/2004 | Senegas |
| 6,783,547 B2 | 8/2004 | Castro |
| 6,790,210 B1 | 9/2004 | Cragg et al. |
| 6,805,697 B1 | 10/2004 | Helm et al. |
| 6,821,277 B2 | 11/2004 | Teitelbaum |
| 6,830,571 B2 | 12/2004 | Lenke et al. |
| 6,875,211 B2 | 4/2005 | Nichols et al. |
| 6,884,243 B2 | 4/2005 | Sellers |
| 6,885,243 B2 | 4/2005 | Burstein et al. |
| 6,899,716 B2 | 5/2005 | Cragg |
| 6,921,403 B2 | 7/2005 | Cragg et al. |
| 7,008,422 B2 | 3/2006 | Foley et al. |
| 7,011,658 B2 * | 3/2006 | Young ............... 606/258 |
| 7,011,660 B2 | 3/2006 | Sherman et al. |
| 7,014,633 B2 | 3/2006 | Cragg |
| 7,060,066 B2 | 6/2006 | Zhao et al. |
| 7,087,058 B2 | 8/2006 | Cragg |
| 7,118,579 B2 | 10/2006 | Michelson |
| 7,118,580 B1 | 10/2006 | Beyersdorff et al. |
| 7,153,281 B2 | 12/2006 | Holmes |
| 7,160,300 B2 | 1/2007 | Jackson |
| 7,232,463 B2 | 6/2007 | Falahee |
| 7,338,527 B2 | 3/2008 | Blatt et al. |
| 7,455,685 B2 | 11/2008 | Justis |
| 7,465,306 B2 | 12/2008 | Pond et al. |
| 7,572,276 B2 | 8/2009 | Lim et al. |
| 7,585,316 B2 | 9/2009 | Trieu |
| 8,197,522 B2 | 6/2012 | Park et al. |
| 8,425,602 B2 | 4/2013 | Guyer et al. |
| 8,512,343 B2 | 8/2013 | Dziedzic et al. |
| 2001/0012938 A1 | 8/2001 | Zucherman |
| 2001/0031965 A1 | 10/2001 | Zucherman et al. |
| 2002/0016595 A1 | 2/2002 | Michelson |
| 2002/0045904 A1 | 4/2002 | Fuss et al. |
| 2002/0049444 A1 * | 4/2002 | Knox ............... 606/61 |
| 2002/0055741 A1 | 5/2002 | Schlapfer et al. |
| 2002/0099386 A1 | 7/2002 | Beger et al. |
| 2002/0143328 A1 | 10/2002 | Shluzas et al. |
| 2002/0161368 A1 | 10/2002 | Foley et al. |
| 2002/0183755 A1 | 12/2002 | Michelson et al. |
| 2002/0188296 A1 | 12/2002 | Michelson |
| 2003/0018389 A1 | 1/2003 | Castro et al. |
| 2003/0074005 A1 | 4/2003 | Roth et al. |
| 2003/0078583 A1 | 4/2003 | Biedermann et al. |
| 2003/0153913 A1 | 8/2003 | Altarac |
| 2003/0187436 A1 * | 10/2003 | Bolger et al. ............... 606/61 |
| 2003/0229347 A1 | 12/2003 | Sherman et al. |
| 2003/0236472 A1 | 12/2003 | Van Hoeck et al. |
| 2004/0030346 A1 | 2/2004 | Frey et al. |
| 2004/0044412 A1 | 3/2004 | Lambrecht et al. |
| 2004/0073216 A1 | 4/2004 | Lieberman |
| 2004/0133207 A1 | 7/2004 | Abdou |
| 2004/0138671 A1 | 7/2004 | Zander et al. |
| 2004/0153070 A1 | 8/2004 | Barker et al. |
| 2004/0167625 A1 | 8/2004 | Beyar et al. |
| 2004/0204712 A1 | 10/2004 | Kolb et al. |
| 2004/0204713 A1 | 10/2004 | Abdou |
| 2005/0004573 A1 | 1/2005 | Abdou |
| 2005/0010227 A1 | 1/2005 | Paul |
| 2005/0021029 A1 | 1/2005 | Trieu et al. |
| 2005/0021031 A1 | 1/2005 | Foley et al. |
| 2005/0021040 A1 | 1/2005 | Bertagnoli |
| 2005/0055031 A1 | 3/2005 | Lim et al. |
| 2005/0085813 A1 | 4/2005 | Spitler et al. |
| 2005/0119747 A1 | 6/2005 | Fabris Monterumici et al. |
| 2005/0131406 A1 | 6/2005 | Reiley et al. |
| 2005/0131421 A1 | 6/2005 | Anderson et al. |
| 2005/0154389 A1 | 7/2005 | Selover et al. |
| 2005/0171540 A1 | 8/2005 | Lim et al. |
| 2005/0177163 A1 | 8/2005 | Abdou |
| 2005/0192589 A1 | 9/2005 | Raymond et al. |
| 2005/0197660 A1 | 9/2005 | Haid et al. |
| 2005/0203512 A1 | 9/2005 | Hawkins et al. |
| 2005/0203533 A1 | 9/2005 | Ferguson et al. |
| 2005/0209694 A1 * | 9/2005 | Loeb ............... 623/17.11 |
| 2005/0215999 A1 | 9/2005 | Birkmeyer et al. |
| 2005/0234449 A1 * | 10/2005 | Aferzon ............... 606/61 |
| 2005/0234451 A1 * | 10/2005 | Markworth ............ 606/61 |
| 2005/0245928 A1 | 11/2005 | Colleran et al. |
| 2005/0261768 A1 | 11/2005 | Trieu |
| 2005/0273120 A1 | 12/2005 | Abdou |
| 2005/0283153 A1 | 12/2005 | Polyner |
| 2005/0288669 A1 | 12/2005 | Abdou |
| 2006/0030839 A1 | 2/2006 | Park et al. |
| 2006/0052870 A1 * | 3/2006 | Ferree ............... 623/17.11 |
| 2006/0074488 A1 | 4/2006 | Abdou |
| 2006/0084986 A1 * | 4/2006 | Grinberg et al. ............. 606/61 |
| 2006/0084988 A1 | 4/2006 | Kim |
| 2006/0111728 A1 * | 5/2006 | Abdou ............... 606/86 |

(56) References Cited

U.S. PATENT DOCUMENTS

| | | |
|---|---|---|
| 2006/0142761 A1 | 6/2006 | Landry et al. |
| 2006/0149238 A1 | 7/2006 | Sherman et al. |
| 2006/0149278 A1 | 7/2006 | Abdou |
| 2006/0167454 A1 | 7/2006 | Ludwig et al. |
| 2006/0184247 A1 | 8/2006 | Edidin et al. |
| 2006/0195102 A1* | 8/2006 | Malandain .................. 606/72 |
| 2006/0217710 A1 | 9/2006 | Abdou |
| 2006/0229614 A1 | 10/2006 | Foley et al. |
| 2006/0229615 A1 | 10/2006 | Abdou |
| 2006/0247630 A1* | 11/2006 | Iott et al. .................... 606/61 |
| 2006/0264942 A1 | 11/2006 | Lim et al. |
| 2006/0276803 A1 | 12/2006 | Salerni |
| 2007/0032790 A1 | 2/2007 | Aschmann et al. |
| 2007/0106383 A1 | 5/2007 | Abdou |
| 2007/0123884 A1 | 5/2007 | Abdou |
| 2007/0151116 A1 | 7/2007 | Malandain |

FOREIGN PATENT DOCUMENTS

| | | |
|---|---|---|
| EP | 0611116 | 8/1994 |
| EP | 1180348 | 2/2002 |
| EP | 1442715 | 8/2004 |
| FR | 2781359 | 1/2000 |
| FR | 2856271 | 12/2004 |
| WO | 2004/032726 | 4/2004 |
| WO | 2004/062482 | 7/2004 |
| WO | 2004/093702 | 11/2004 |
| WO | 2005/122922 | 12/2005 |
| WO | 2006/041963 | 4/2006 |
| WO | WO 2006/041963 | 4/2006 |
| WO | 2006/058221 | 6/2006 |
| WO | WO 2006/058221 | 6/2006 |
| WO | 2006/089292 | 8/2006 |
| WO | 2006/096756 | 9/2006 |
| WO | PCT/US2006/39491 | 10/2006 |
| WO | WO 2007/041648 | 4/2007 |
| WO | WO 2007/044705 | 4/2007 |
| WO | WO 2007/044836 | 4/2007 |
| WO | WO 2007/056516 | 5/2007 |
| WO | WO 2007/059207 | 5/2007 |
| WO | WO 2005/077288 | 8/2008 |

OTHER PUBLICATIONS

Derwent English abstract for FR2781359, published Jan. 28, 2000 entitled: "Osteosynthesis frame for spinal surgery has rod with clamps to hold cross bars with anchor screws," Accession Nbr. 9867555 [351].

Derwent English abstract for FR2856271, published Dec. 24, 2004 entitled: "Osteo-synthesis vertebral column plate, has connection head integrated with plate and moveable in three directions of space so as to adapt itself to connection rod, and including opening to facilitate introduction of rod," Accession Nbr. 14694557 [351].

* cited by examiner

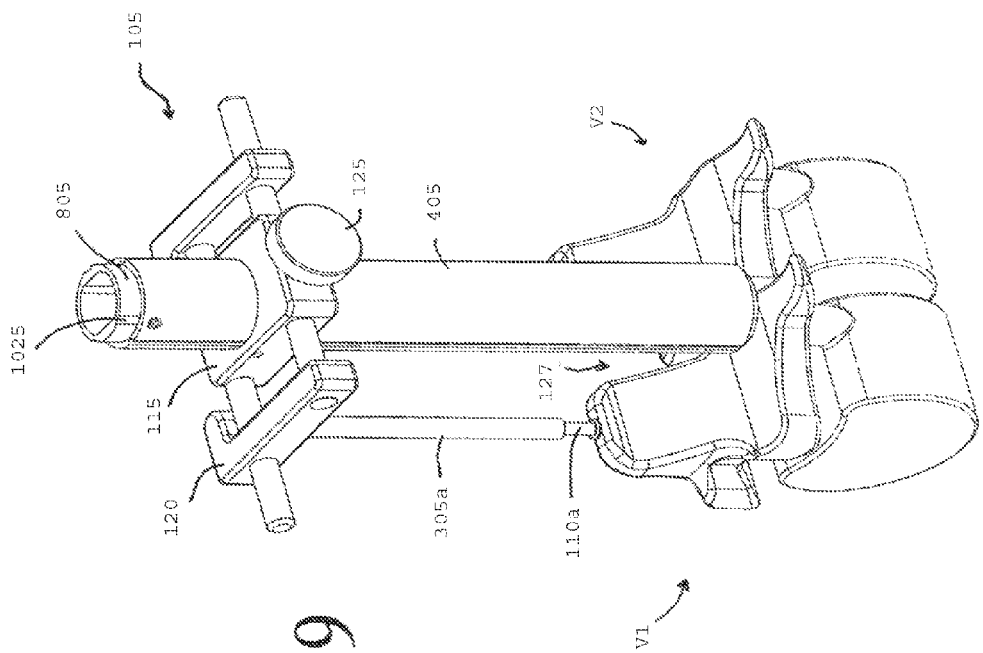

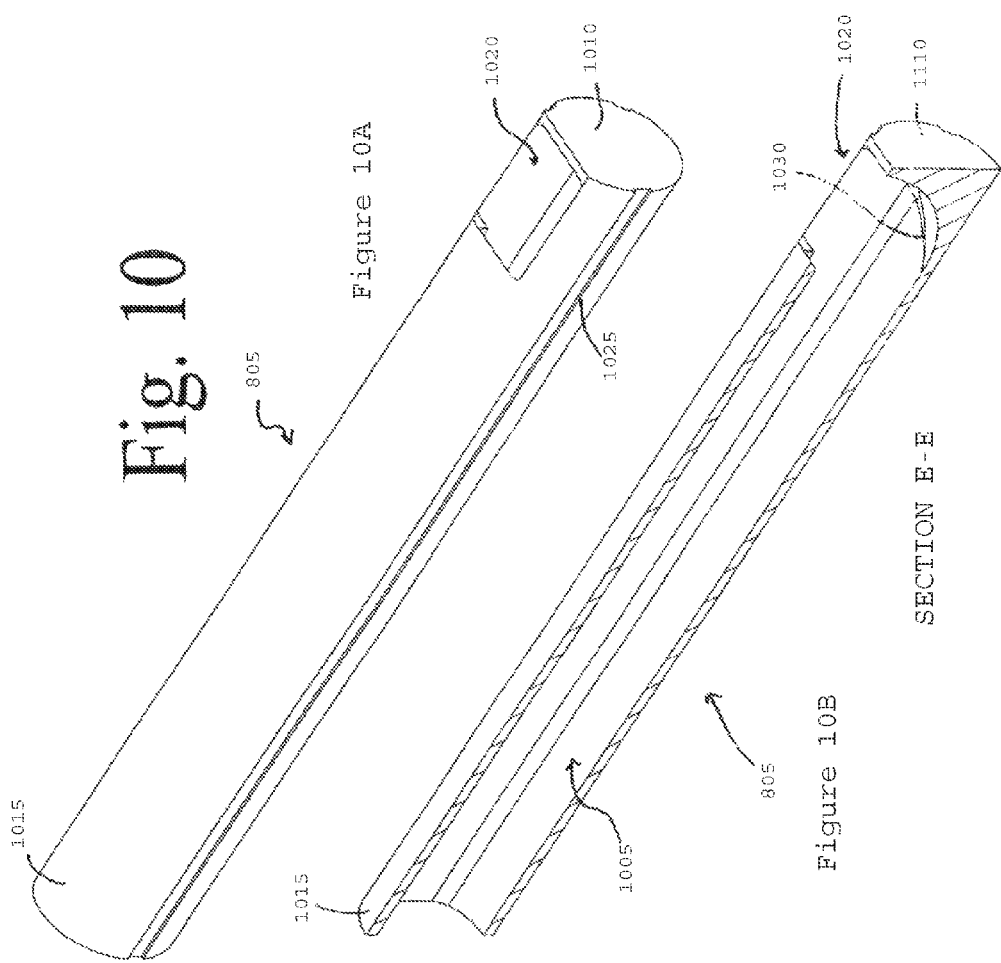

section E-E

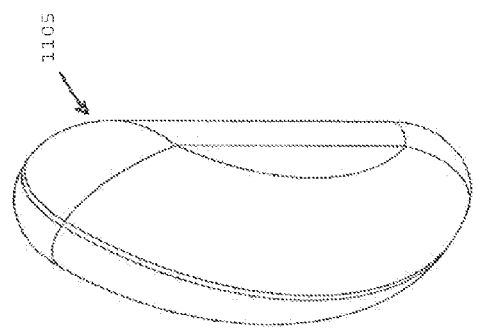
Fig. 11A
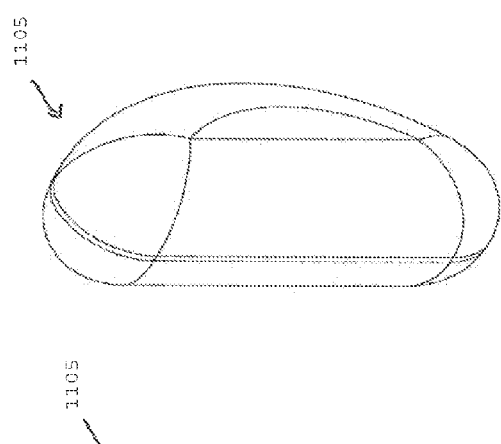
Fig. 11B
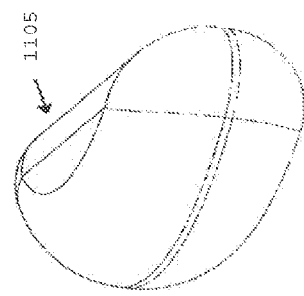
Fig. 11C
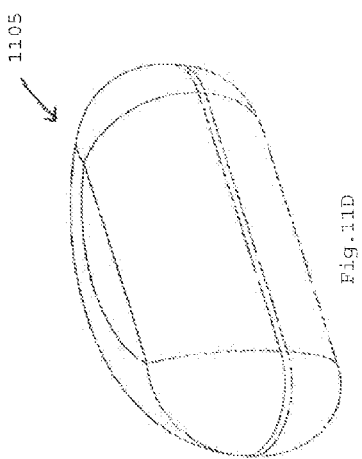
Fig. 11D
Fig. 11

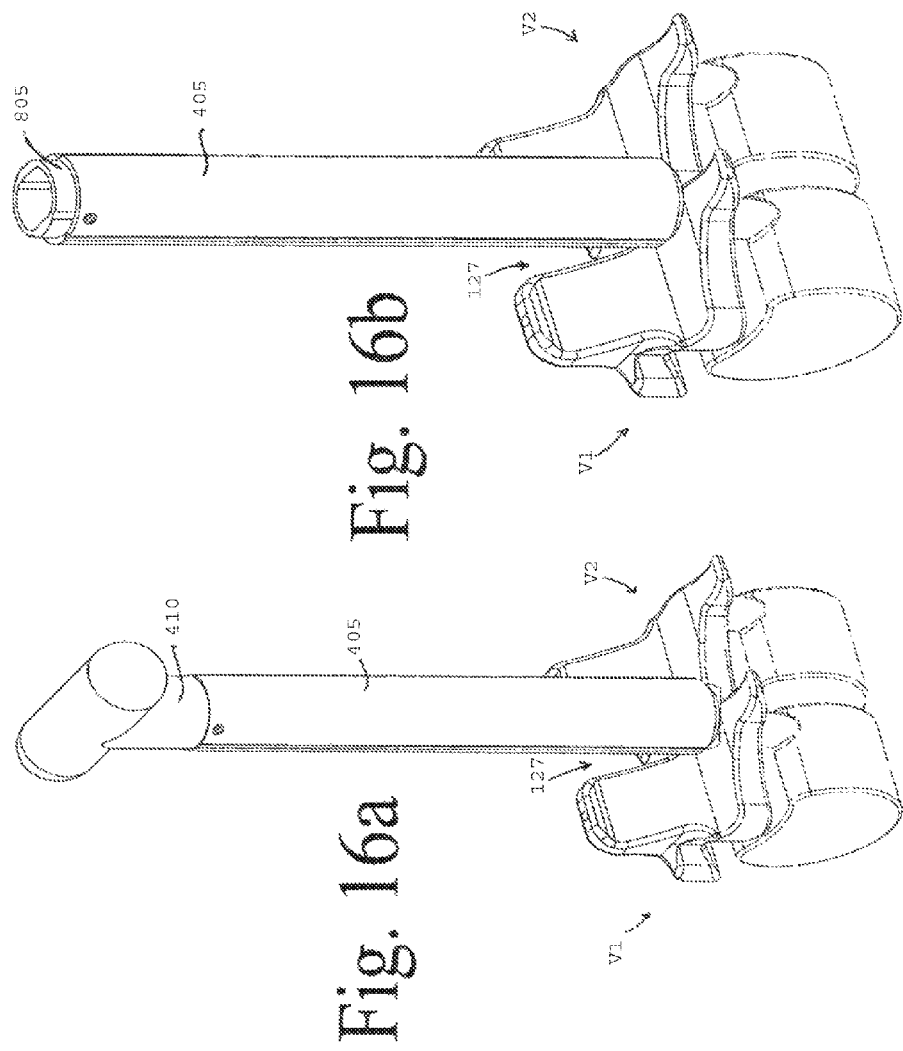

DEVICES AND METHODS FOR INTER-VERTEBRAL ORTHOPEDIC DEVICE PLACEMENT

REFERENCE TO PRIORITY DOCUMENT

This application claims priority of co-owned U.S. Provisional Patent Application Ser. No. 60/724,632, filed Oct. 7, 2005. Priority of the aforementioned filing date is hereby claimed and the disclosure of the Provisional Patent Application is hereby incorporated by reference in its entirety.

This application is a continuation-in-part of co-owned U.S. Patent Application Ser. No. 11/286,152 tiled Nov. 23, 2005, which is published as U.S. Patent Application Publication No. 2006/0149278 on Jul. 6, 2006, and patented as U.S. Pat No. 8.172.855 on May 8, 2012.

This application also is related to co-owned International Application Serial No. PCT/US2005/042757 filed on Nov. 23. 2005, which is published as International Application Publication No. WO2006/058221 on Jun. 1, 2006.

Where permitted, the subject matter of each of the above noted provisional application, application and international application is incorporated by refrence in its entirety by reference thereto.

BACKGROUND

The present disclosure relates to devices and methods that permit implantation of an orthopedic device between skeletal segments using minimally invasive surgery. The implanted devices are then used to adjust and maintain the spatial relationship(s) of adjacent bones. Depending on the implant design, the motion between the skeletal segments can be increased, modified, limited or completely immobilized.

Progressive constriction of the central canal within the spinal column is a predictable consequence of aging. As the spinal canal narrows, the nerve elements that reside within it become progressively more crowded. Eventually, the canal dimensions become sufficiently small so as to significantly compress the nerve elements and produce pain, weakness, sensory changes, clumsiness and other manifestations of nervous system dysfunction.

Constriction of the canal within the lumbar spine is termed lumbar stenosis. This condition is very common in the elderly and causes a significant proportion of the low back pain, lower extremity pain, lower extremity weakness, limitation of mobility and the high disability rates that afflict this age group. The traditional treatment for this condition has been the surgical removal of the bone and ligamentous structures that constrict the spinal canal. Despite advances in surgical technique, spinal decompression surgery can be an extensive operation with risks of complication from the actual surgical procedure and the general anesthetic that is required to perform it. Since many of these elderly patients are in frail health, the risk of developing significant peri-operative medical problems remains high.

In addition, the traditional treatment of surgical resection of spinal structures may relieve the neural compression but lead to spinal instability in a substantial minority of patients. That is, removal of the tissues that compress the nerves may cause the spinal vertebrae to move in an abnormal fashion and produce pain. Should instability develop, it would require additional and even more extensive surgery in order to re-establish spinal stability. Because of these issues, elderly patients with lumbar stenosis must often choose between living the remaining years in significant pain or enduring the potential life-threatening complications of open spinal decompression surgery.

Recently, lumbar stenosis has been treated by the distraction—instead of resection—of those tissues that compress the spinal nerves. In this approach, an implantable device is placed between the spinous processes of the vertebral bodies at the stenotic level in order to limit the extent of bone contact during spinal extension. Since encroachment upon the nerve elements occurs most commonly and severely in extension, this treatment strategy produces an effective increase in the size of the spinal canal by limiting the amount of spinal extension. In effect, the distraction of the spinous processes changes the local bony anatomy and decompresses the nerves at the distracted levels.

A number of devices that utilize this strategy have been disclosed. U.S. Pat. Nos. 6,451,020; 6,695,842; 5,609,634; 5,645,599; 6,451,019; 6,761,720; 6,332,882; 6,419,676; 6,514,256; 6,699,246 and others illustrate various spinous process distractors. Unfortunately, the placement of these devices requires exposure of the spinous processes and the posterior aspect of the spinal column. Thus, these operations still present a significant risk of peri-operative complications in this frail patient population.

SUMMARY

It would be desirable to achieve an improved method for the placement of an orthopedic device between the spinous processes of adjacent spinal segments. A workable method of minimally invasive and/or percutaneous delivery would reduce the surgical risks of these procedures and significantly increase the usefulness of these spinous process distractors. This application discloses devices for the percutaneous placement of inter-spinous process implants. The methods of use disclosed herein provide reliable approaches that maximize the likelihood of optimal device placement and obviate the need for open surgery.

The present disclosure relates to devices and methods adapted to accurately place an orthopedic device between adjacent spinous processes. The technique employs a percutaneous approach and constitutes a minimally invasive method of delivery.

In one aspect, the patient is placed on his side or in the prone position. The hips and knees are flexed. The disclosed procedure is performed under x-ray guidance and the target level is identified radiographically. Bone screws are percutaneously inserted into the spinous processes of the upper and lower vertebrae of the stenotic site. A distractor is placed onto the two screws and a guide tube (with inner trocar) is placed through a distractor platform and percutaneously positioned under x-ray guidance so that the distal end of the guide tube rests immediately lateral to the space between the spinous processes. Alternatively, the procedure is performed under direct visualization using minimally invasive surgery. The inner trocar is removed and an insertion tube is placed though the guide tube. The implant is placed into the insertion tube and guided into position between the two spinous processes. In one embodiment, this is accomplished by a curvilinear guide at the distal end of the insertion tube.

In another embodiment, the distraction platform is not used and a guide tube is percutaneously placed into position immediately lateral to the space between the spinous processes under X-ray guidance. The inner trocar is removed and the insertion tube is used to deliver the implant as described above. In another embodiment, guide tubes are placed on each side of the space between the spinous processes. After trocar removal, insertion tubes are placed and the implant is guided into the interspinous space from one side or the other.

In another embodiment, a different distraction platform is employed. In this version, the platform bore used to position the guide tube is placed at or near the vertebral midline. The implant is advanced in a substantially straight trajectory through the ligament between the spinous processes and directly into the implantation site.

The placement system described herein provides an easy and reliable way of placing an orthopedic device between the spinous processes of two adjacent vertebrae. Using this method, the implant can be placed rapidly, precisely, with a few small skin incisions and a minimized amount of tissue dissection. The method permits minimally-invasive device placement using only local anesthesia into those afflicted patients who are at least able to withstand the stress of open surgical intervention.

Other features and advantages should be apparent from the following description of various embodiments, which illustrate, by way of example, the principles of the disclosed devices and methods.

BRIEF DESCRIPTION OF THE DRAWINGS

FIG. 9 shows the insertion member mounted in the guide tube, which is mounted on the platform.

FIG. 10A shows a perspective view of the insertion tube.

FIG. 10B shows a perspective, cross-sectional view of the insertion tube.

FIGS. 11A-11D show various views of an implant.

FIGS. 16A and 16B show another embodiment of an implantation procedure.

DETAILED DESCRIPTION

Disclosed are devices and methods for the placement of an orthopedic implant between skeletal segments (such as vertebrae) using limited surgical dissection. The implanted devices are used to adjust and maintain the spatial relationship(s) of adjacent bones.

Figure 1:
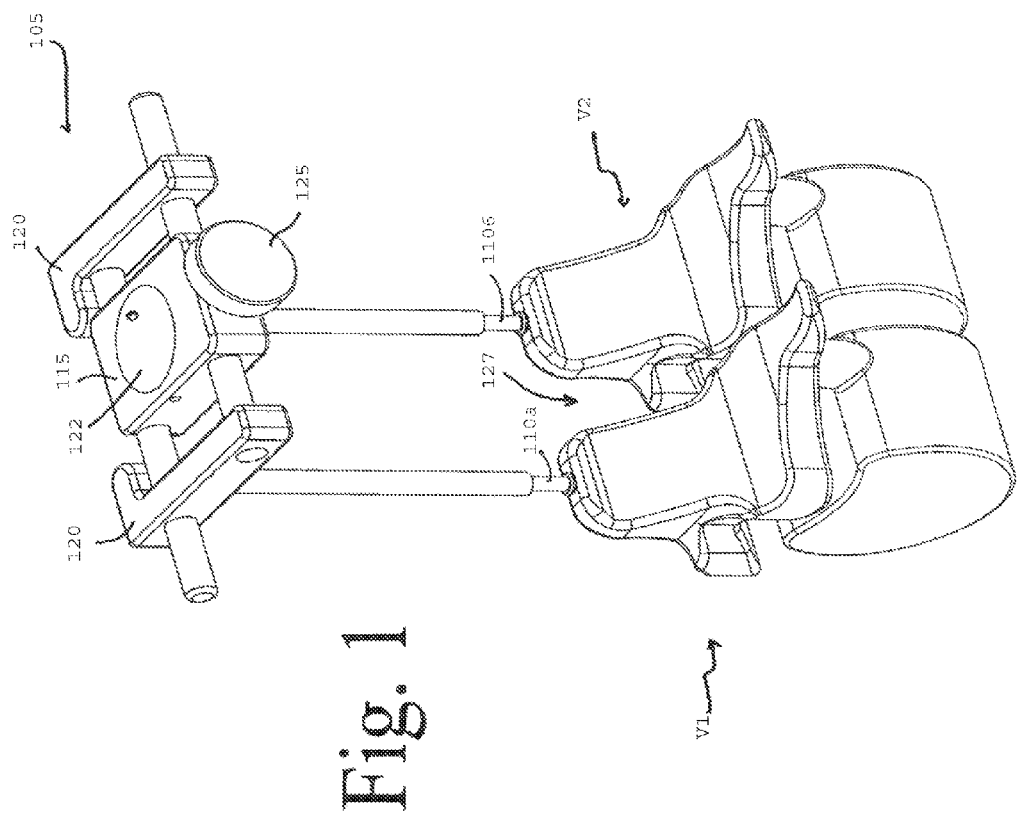
FIG. 1 shows a perspective view of a platform of an implantation device for implanting an orthopedic device between skeletal segments.

FIG. 1 shows a perspective view of a platform device that is used to implant an orthopedic device between skeletal segments, such as between a first vertebral body V1 and a second vertebral body V2. For clarity of illustration, the vertebral bodies are represented schematically and those skilled in the art will appreciate that actual vertebral bodies include anatomical details not shown in FIG. 1. Moreover, although described in the context of being used with vertebrae, it should be appreciated that the implantation device and associated methods can also be used with other skeletal segments. For clarity of illustration, certain anatomical details, such as the patient's skin, are not shown in the figures.

With reference to FIG. 1, the implantation device generally includes a platform 105 that is removably mounted onto elongated distraction screws 110a and 110b (collectively screws 110). The platform 105 includes a movably adjustable mounting member 115 having a bore 122 that receives tools for guiding and inserting an implant into a space 127 between adjacent vertebrae. While not illustrated for simplicity, an additional instrument can be used to separate and retain sides 120 of the platform 105 and thereby distract the space 127 between the two spinous processes or vertebrae in the longitudinal plane. Alternatively, a rack-like ratcheting member can be added to the platform 105 in order to distract and maintain the distracted position of the two vertebrae. Further, distraction screws 110 can be also used to alter the vertebral alignment in the horizontal plane. Thus, the screws 110 and the platform 105 can be used to actuate, manipulate and/or move the vertebral bodies V1, V2 relative to one another so as to achieve a desired spatial relationship. With the vertebrae retained by distraction screws 110 and platform 105, the intended implant placement site can be defined relative to the position of the screws 110, the position of the platform 105 and/or the spatial relationship between them. The implant is then guided to the intended implantation site based on these defined spatial positions.

Figure 2:
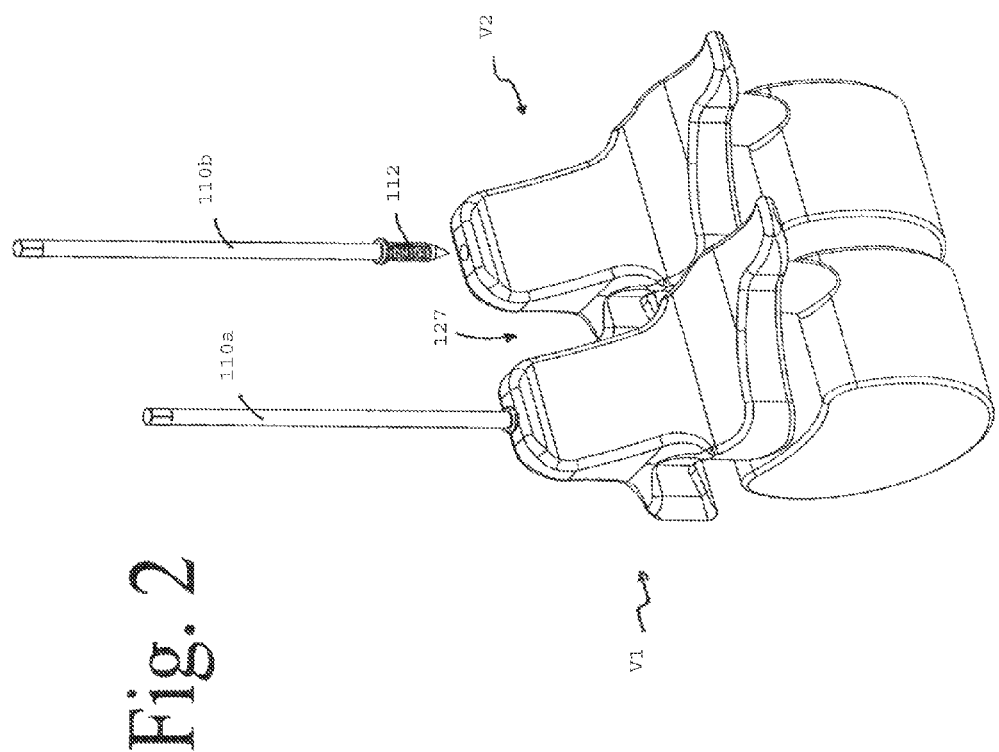
FIG. 2 shows a pair of distraction screws attached to two vertebrae prior to mounting of the platform thereon.

FIG. 2 shows the two vertebrae prior to mounting of the platform 105. The distraction screws 110a and 110b are anchored onto the spinous processes of vertebrae V1 and V2, respectively, such that each distraction screw 110 is attached at its distal end to a separate vertebra. In this regard, the distal end of each screw 110 can include a structure for attaching to the spinous process, such as a threaded shank 112.

Figure 3:
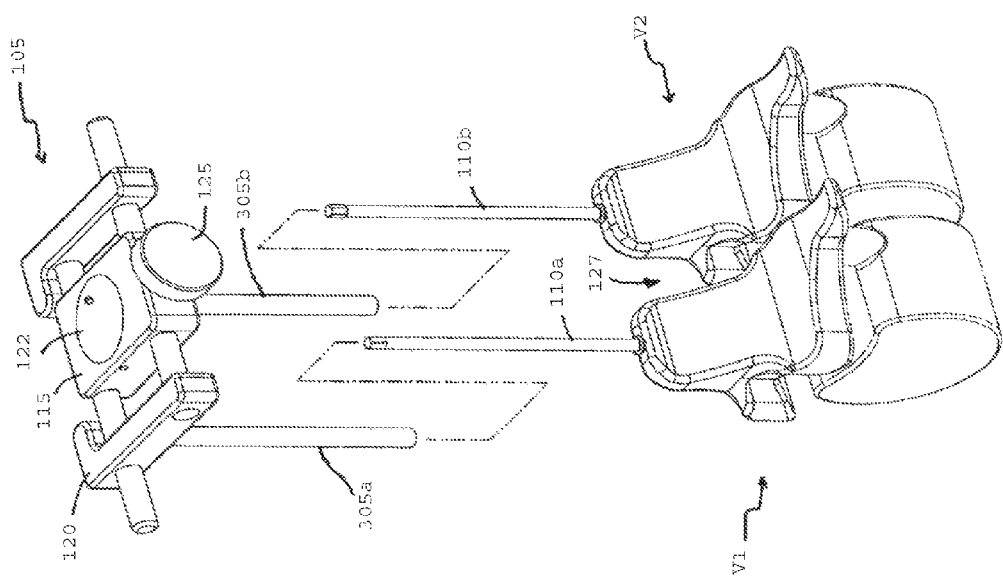
FIG. 3 shows how the platform mounts onto the distraction screws.

FIG. 3 shows how the platform 105 mounts onto the distraction screws 110. The platform 105 includes a pair of elongated sleeves 305a and 305b that are sized and positioned to receive the distraction screws 110a and 110b, respectively, within internal shafts of the sleeves. When the sleeves 305 are inserted over the distraction screws 110, the platform 105 is mounted over the vertebrae as shown in FIG. 1.

Figure 4:
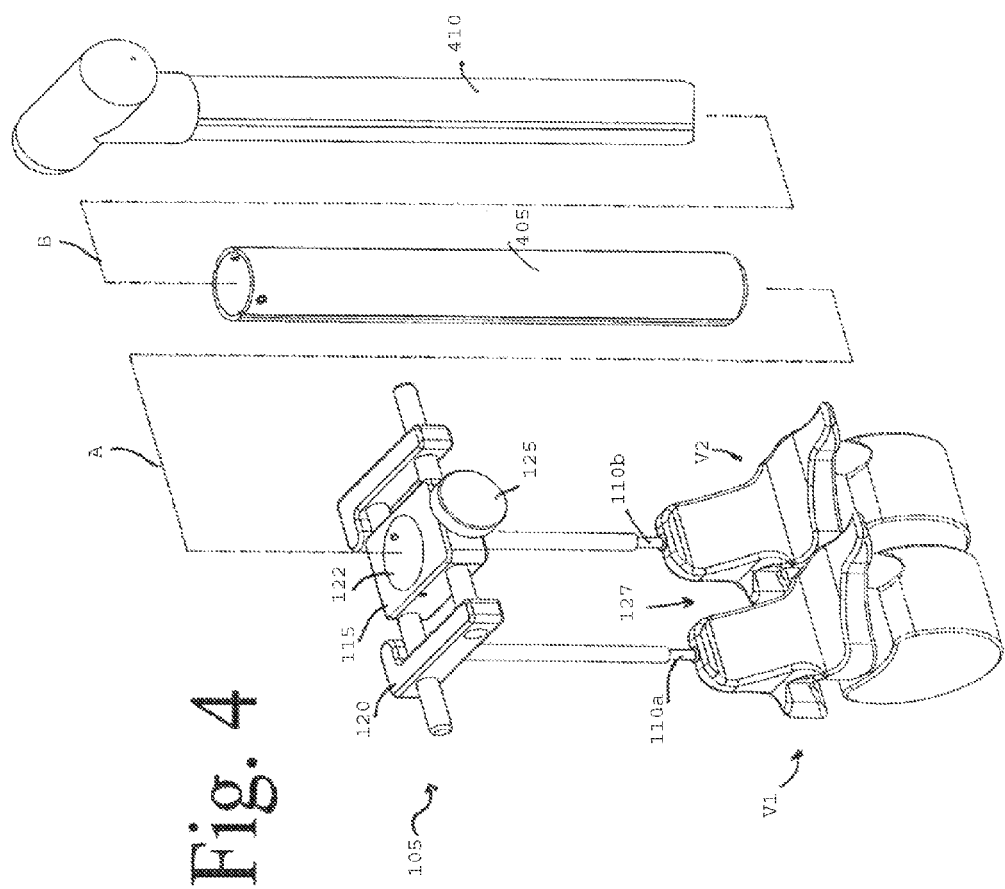
FIG. 4 shows the platform device, a guide tube, and an inner trocar.
Figure 5:
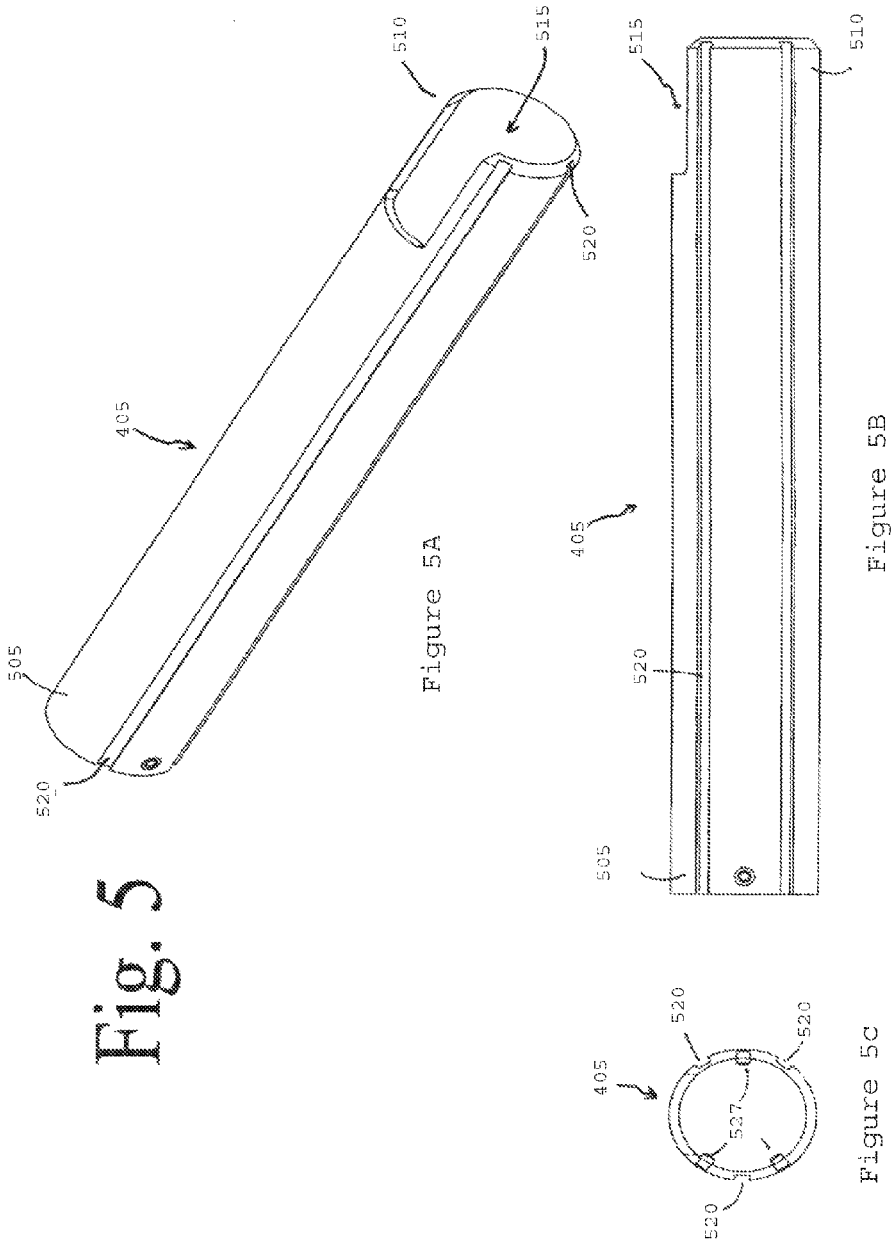
FIGS. 5A-5C show various views of the guide tube.

With reference to FIG. 4, the implantation device further includes a guide tube 405 and a trocar 410. The guide tube 405 is sized and shaped to be inserted into the bore 122, as represented by the line A in FIG. 4. FIG. 5A shows a perspective view of the guide tube 405, FIG. 5B shows a side view of the guide tube 405, and FIG. 5C shows an end-wise view of the guide tube 405. The guide tube has a proximal end 505 and a distal end 510. The guide tube 405 is hollow such that an internal shaft extends therethrough with the internal shaft opening at the proximal 505 and distal ends 510 of the guide tube 405. A slot-like opening 515 is located at the distal end 510 along one side of the guide tube 405.

The guide tube 405 includes alignment means 520, such as indentations 520, on its outer wall that are intended to interact with the complimentary protrusions in the mounting member 115. The indentations 520 permit placement of the guide tube 405 in a predetermined orientation relative to the mounting member 115 of the platform 105. In this way, the guide tube 405 is always placed with the distal opening 515 facing the space 127 between the spinous processes, as described below. Likewise, the guide tube 405 has protrusions 527 on its inner wall that compliment indentations 1025 on the outer wall of an insertion tube 805 (described below). These features ensure that the distal openings of both tubes face the space between the spinous processes, as described in more detail below.

Figure 6:
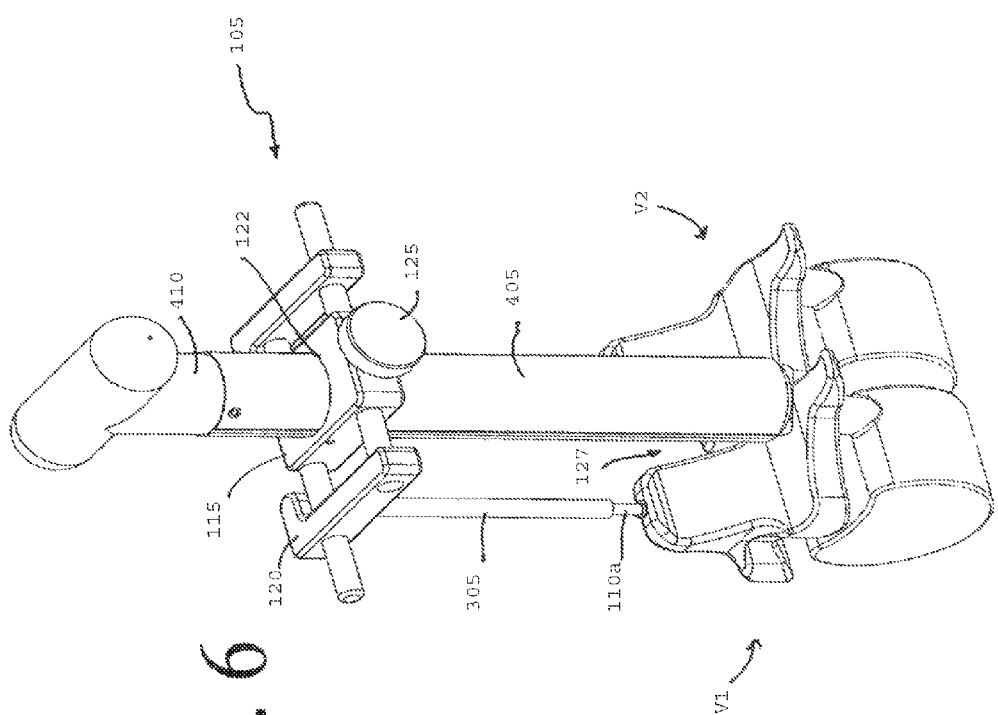
FIG. 6 shows the guide tube and a trocar collectively positioned within the platform.

With reference again to FIG. 4, the trocar 410 is sized and shaped to be inserted into the guide tube 405, as represented by the line B. FIG. 6 shows the guide tube 405 and trocar 410 collectively positioned within the bore 122 of the platform 105. That is, the trocar 410 is positioned within the guide tube 405 and the guide tube 405 is positioned within the bore 122. When positioned as such, the opening 515 (FIGS. 5A, 5B) is positioned adjacent to and oriented toward the space between the vertebrae V1 and V2.

Figure 7:
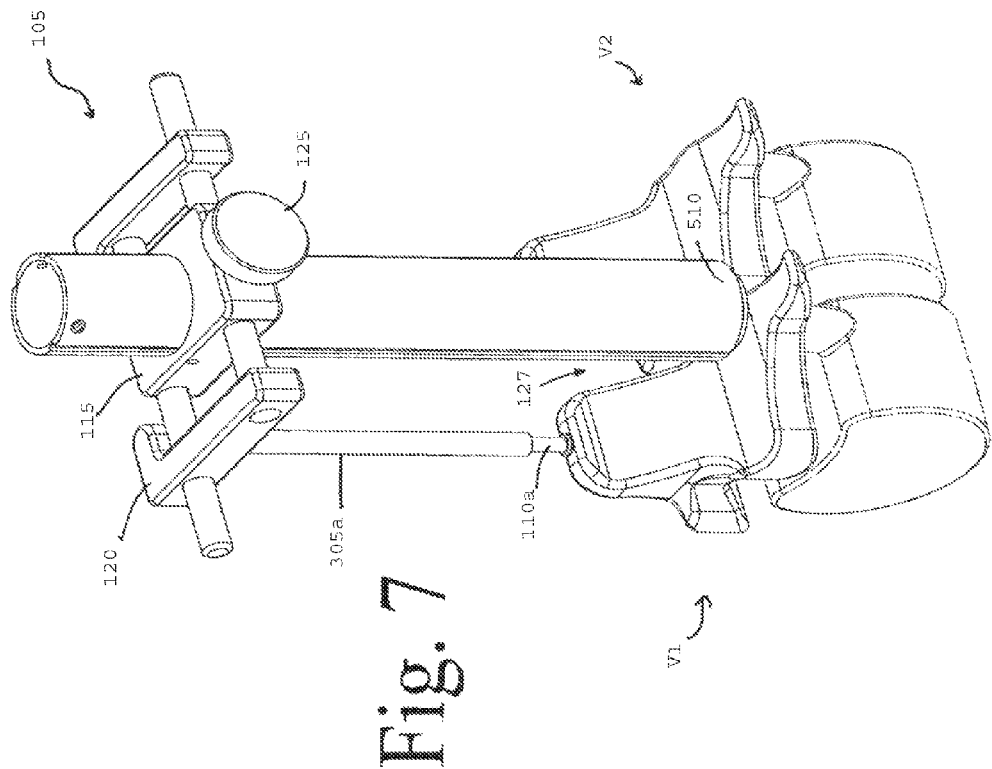
FIG. 7 shows the guide tube mounted on the platform after the trocar has been removed.
Figure 8:
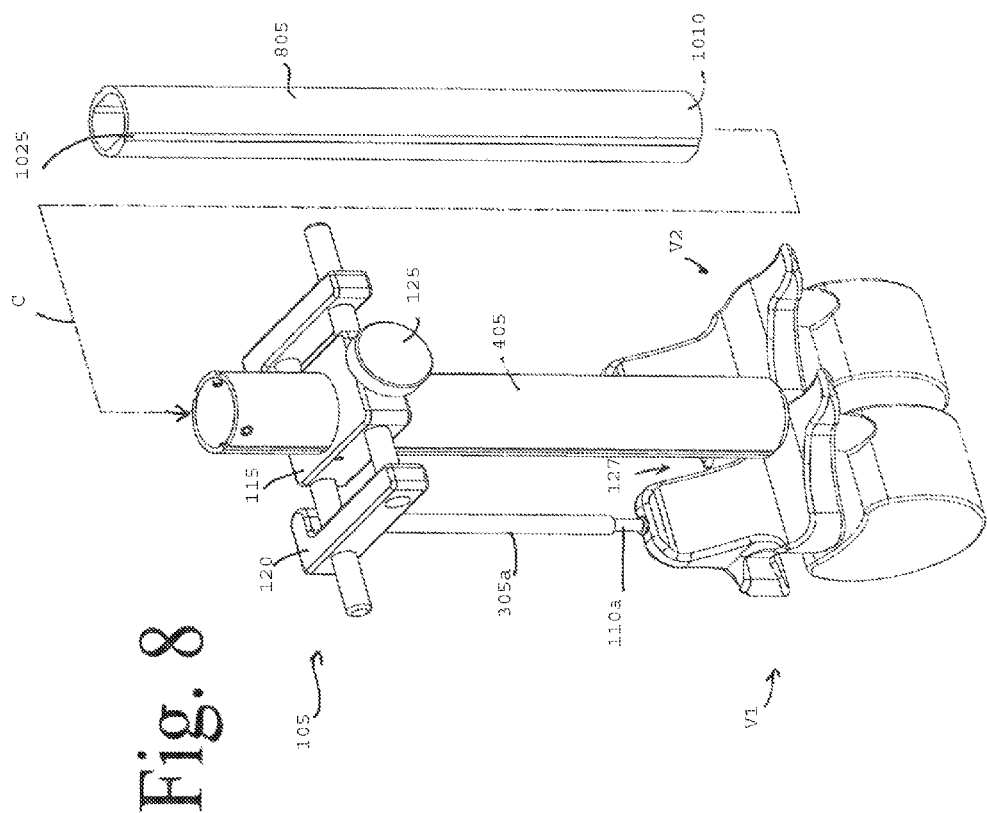
FIG. 8 shows an insertion member prior to insertion into the guide tube.

The trocar 410 can be removed from the guide tube 405 while the guide tube 405 remains mounted in the mounting member 115 of the platform 105. FIG. 7 shows the guide tube 405 mounted on the platform 105 after the trocar 410 has been removed from the guide tube 405. With reference now to FIG. 8, the implantation device further includes an insertion tube 805 that is sized and shaped to insert into the guide tube 405, as represented by the line C in FIG. 8. FIG. 9 shows the insertion member 805 mounted in the guide tube 405, which is mounted on the mounting member 115 of the platform 105.

The insertion tube 805 is now described in more detail with reference to FIGS. 10A-10E. The insertion tube 805 is adapted to receive and guide an implant into a space between the vertebrae, as described below. The insertion tube 805 is elongated and includes an passageway 1005 that opens at both a distal end 1010 and proximal end 1015 of the insertion tube 805. The distal opening 1020 is positioned on a side of the insertion tube 805. As mentioned, the insertion tube 805 includes alignment means, such as indentations 1025, on its outer wall. The indentations 1025 are sized and shaped to mate with the protrusions 527 (FIG. 5C) on the inner wall of the guide tube 405. In this manner, the distal opening 1020 of the insertion tube 805 aligns with the distal opening 515 of the guide tube 405 when the insertion tube 805 is positioned within the guide tube 405.

Figure 10C:
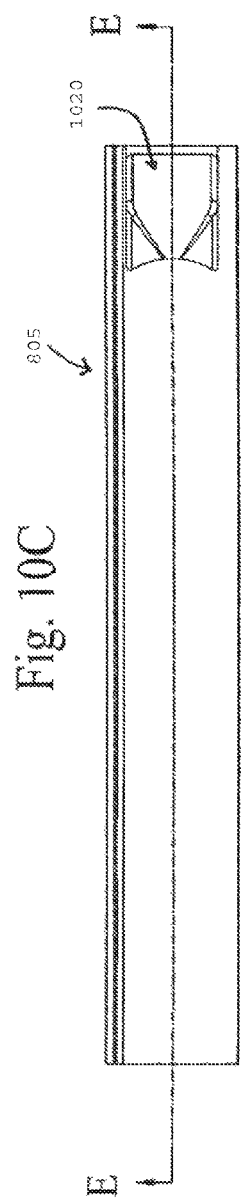
FIG. 10C shows a first side view of the insertion tube.
Figure 10D:
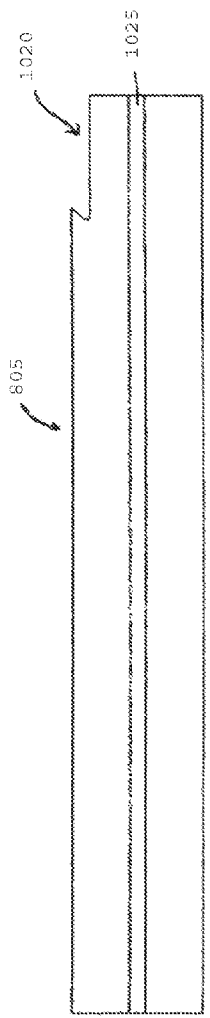
FIG. 10D shows a second side view of the insertion tube.
Figure 10E:
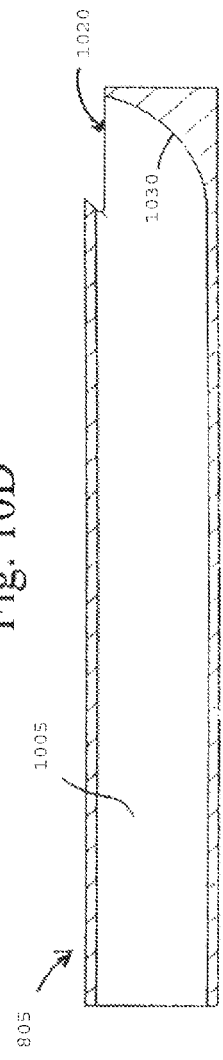
FIG. 10E shows a cross-sectional side view of the insertion tube along line E-E of FIG. 10C.

With reference to FIGS. 10B and 10E, the internal passageway 1005 of the insertion tube 805 includes a guide ramp 1030 or other such structure adjacent the opening 1020. The guide ramp 1030 is adapted to guide an implant toward the opening 1020 as the implant is moved down the passageway 1005, as described below. It should be appreciated that other structures can be used to guide the implant toward the opening 1020. In one embodiment, the ramp 1030 has a shape that compliments the shape of an implant that is guided through the insertion tube 805.

FIGS. 11A-11D show various views of an exemplary implant 1105 that can be used with the implantation device described herein. The implant 1105 is sized and shaped to slidably fit within the passageway 1005 (FIG. 10B) of the insertion tube 805. The implant 1105 can be, for example, a device intended to preserve vertebral movement or a fusion device that immobilizes vertebral movement. For clarity of illustration, structural details of the implant 1105 are not shown in FIGS. 11A-11D, although it should be appreciated that the implant 1105 can have a variety of structures, shapes and sizes.

An exemplary method of use for the implantation device is now described. Pursuant to the method, the platform 105, bore 122, and/or the guide 405 and insertion tubes 805 are positioned and aligned in a defined relationship relative to the intended implant placement site. The platform 105 can be movable or stationary or it can change between a movable and stationary state. The guide tube 405 and/or insertion tube 805 can be percutaneously positioned into a defined spatial relationship relative to the intended implant placement site based on their interaction with the platform 105.

With reference to FIG. 2, the distraction screws 110 are first anchored onto the vertebral bodies. Next, as shown in FIG. 3, the platform 105 is mounted onto the distraction screws 110 by sliding the sleeves 305 over the distraction screws 110.

Figure 15:
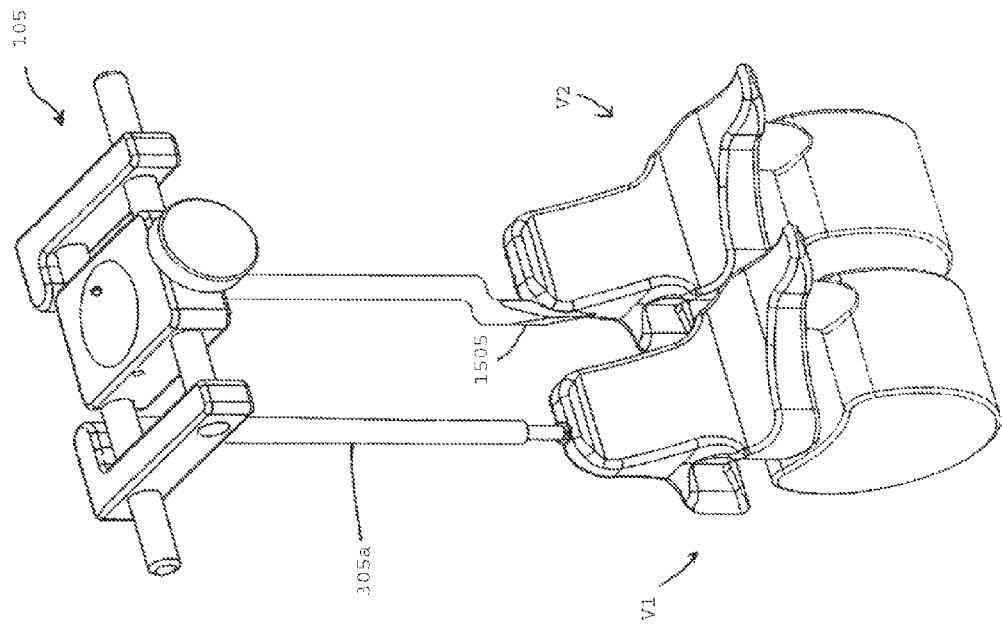
FIG. 15 shows an additional embodiment of the implantation platform.

It should be appreciated that the platform 105 can be attached to the vertebrae by other means. For example, the platform 105 can attach onto one or more spinous process using a clamp or spinous process-encircling attachment. Moreover, the platform 105 can be also attached to a first vertebra using a single distraction, clamp or encircling attachment while a secondary post rests within the inter-spinous space (that is, the space between the two spinous processes) and abuts the spinous process of the second vertebra. An example of the method is shown in FIG. 15. Alternatively, the platform 105 can contain one or more attachments that are positioned within the inter-spinous space and that can attach onto or abut one or both spinous process. Finally, the platform can attach onto a single vertebrae that would forgo the ability to manipulate the spatial relationship between the vertebrae but retain the implant placement function. It should be appreciated that the preceding are exemplary embodiments and do not constitute an exhaustive list of potential platforms.

After the platform 105 is mounted, the mounting member 115 of the platform 105 is then movably adjusted to a position at the level of the space between the vertebral bodies (i.e., the spinous processes) under x-ray guidance and then locked in position, such as by using a locking screw 125 or other locking means. With reference to FIG. 4, the trocar 410 is then inserted into the guide tube 405 and both are placed through the bore 122 of the mounting member 115, as shown in FIG. 6. The guide tube 405 and the trocar 410 have been pushed through the skin such that their distal ends approach toward the vertebral bodies. At this stage in the procedure, the distal opening 515 (FIG. 5A) of the guide tube 405 is positioned such that it is adjacent to and opens toward the space 127 between the vertebral bodies. The trocar 410 is then removed from the guide tube 405 such that the empty guide tube 405 is mounted on the platform 105 with the distal end 510 of the guide tube 405 is adjacent to the space 127 between the vertebral bodies V1, V2, as shown in FIG. 7.

Figure 12:
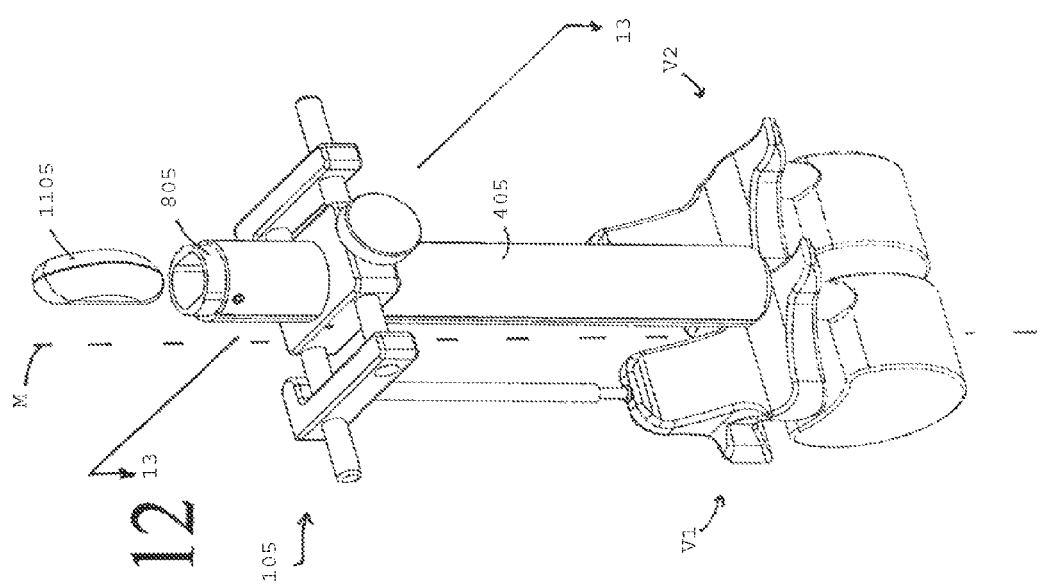
FIG. 12 shows an implant being inserted into a proximal opening of the insertion tube, which is positioned inside the guide tube.
Figure 13:
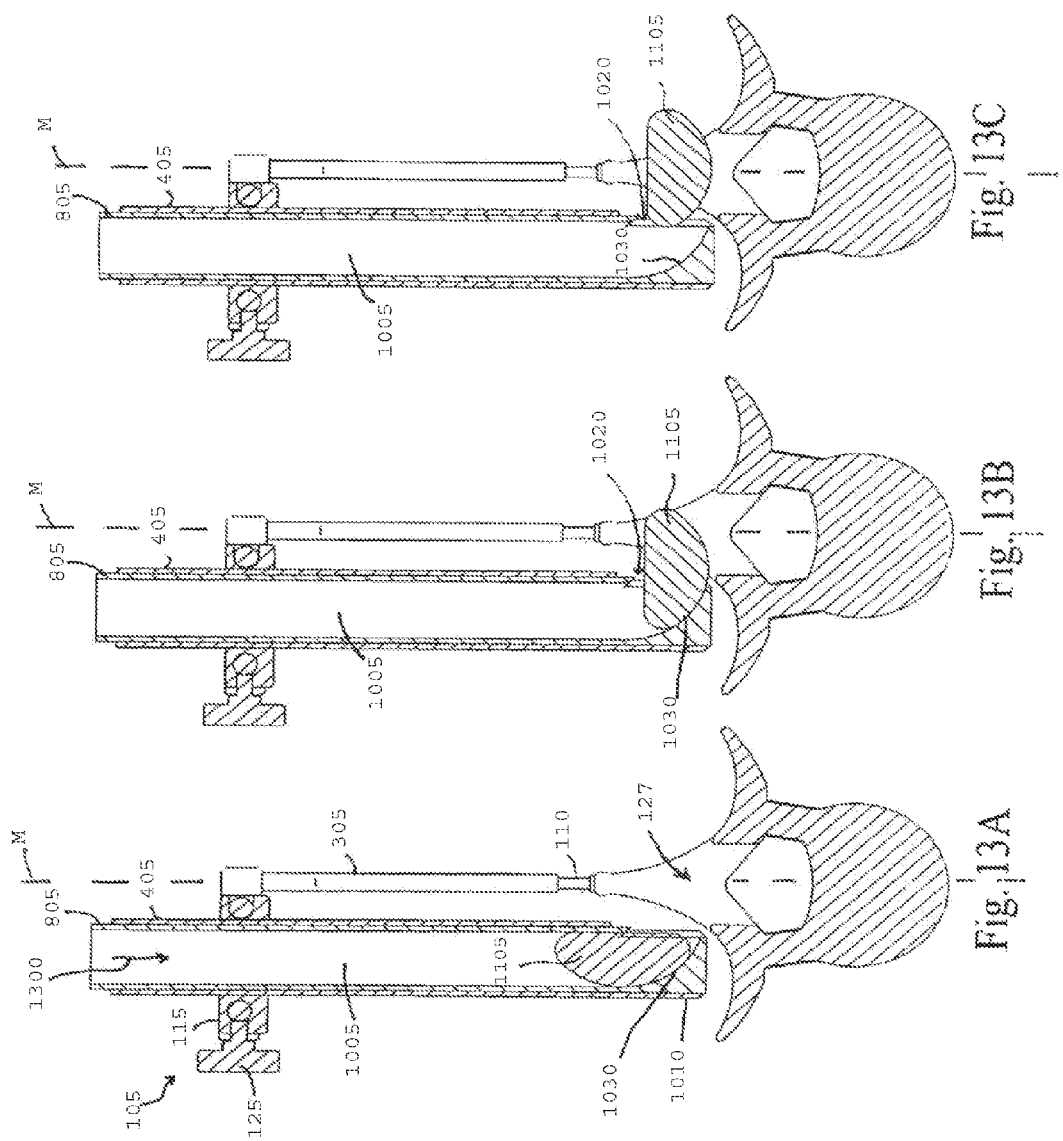
FIGS. 13A-13C show how the implant passes through the insertion tube and into an interspinous position.

Insertion tube 805 is inserted into the guide tube 405, as shown in FIG. 8, and advanced through the tissues until the distal end 1010 is positioned adjacent to the desired implant placement site. The distal opening 1020 (FIG. 10A) of the insertion tube 805 is aligned with the distal opening 515 of the guide tube 405. Both openings 515, 1020 are positioned such that they are open toward the space 127 between the vertebral bodies. Implant 1105 is inserted into the proximal opening of the insertion tube 805, as shown in FIG. 12. A pusher can be used to advance the implant 1105 in a direction 1300 through the inner passageway 1005 of the insertion tube 805 and toward the desired position in inter-spinous space 127. FIGS. 13A-13C show how the implant 1105 passes through the insertion tube 805 and into an interspinous space 127. As shown in FIG. 13A, the implant 1105 has been pushed through the passageway 1005 to a position near the distal end 1010 of the insertion tube 805.

As mentioned, the guide ramp 1030 is adapted to guide the implant 1105 toward the opening 1020 and toward the inter-spinous space 127. With reference to FIGS. 13B and 13C, the implant 1105 is pushed out of the opening 1020 and into the desired location within the inter-spinous space 127. After implant placement, all of the implantation devices are removed but the implant 1105 is retained.

Figure 14:
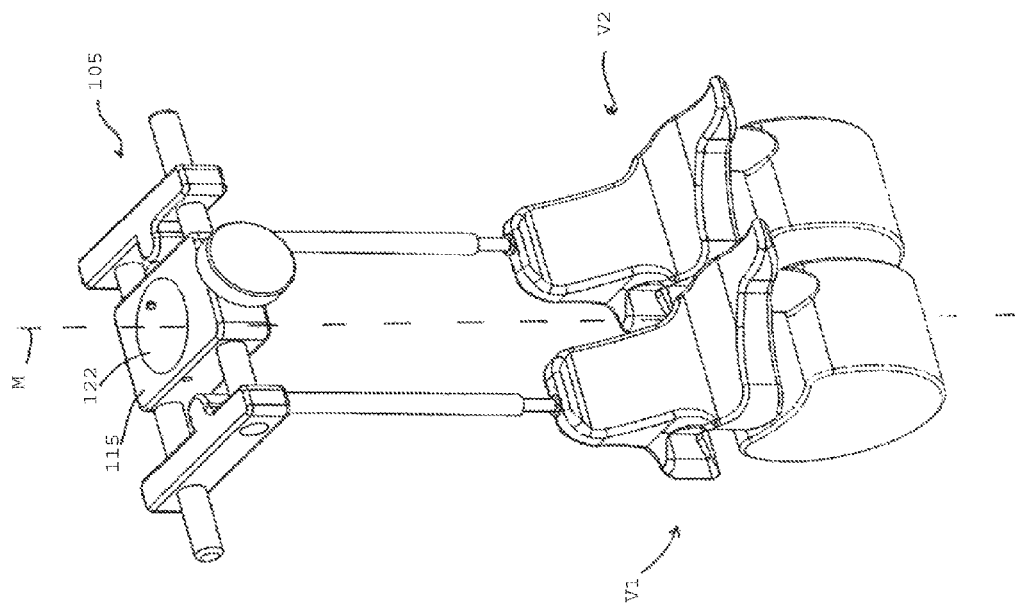
FIG. 14 shows another embodiment of the implantation platform.

In the embodiments described above, the insertion tube 805 is positioned within the platform 105 along an axis that is offset from the vertical midline M such that the implant 1105 approaches the implant site from the side. In another embodiment, the platform bore 122 that is used to position the insertion tube 805 is placed at or near the vertebral midline M. An example of this platform embodiment is shown in FIG. 14. In this procedure, the implant 1105 is advanced in a substantially straight trajectory through the ligament (not visible) between the spinous processes and directly into the implantation site. Moreover, the insertion tube 805 has no guide ramp 1030 so as to provide the desired straight implant placement trajectory through the insertion tube 805.

FIGS. 16A and 16B show another embodiment of an implantation procedure. In this embodiment, the distraction platform 105 is not employed. During implantation, the guide tube 405 and the trocar 410 are positioned adjacent to the interspinous space 127 under X-ray or direct visual guidance. The guide tube 405 is positioned over a series of progressively larger tubes. Once positioned, the insertion tube 805 is passed into the guide tube 405. The implant 1105 is then guided and placed into the interspinous space via the insertion tube 805 in the manner described above. In another embodiment, two or more tubes can be placed on each side of the interspinous space and the implant 1105 can be passed between the two tubes into the implantation site.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed is:

1. A method for implantation of an orthopedic implant into an interspinous space between spinous processes of a first and a second immediately adjacent vertebral bones, comprising:
   providing an implant insertion tube having an elongated body and extending along a first axis from a proximal aperture to a distal aperture, wherein the elongated body has an internal bore that connects the proximal and distal apertures and wherein the internal bore is sized and shaped to permit passage of the orthopedic implant from the proximal aperture to the distal aperture;
   positioning an implant insertion tube at a midline of the vertebral bones and posterior to the interspinous space that is between the spinous processes of the first and second vertebral bones, wherein the first axis of the implant insertion tube is aligned parallel with the plane of the vertebral midline;
   advancing the orthopedic implant through the internal bore of the implant insertion tube and into the interspinous space; and
   removing the implant insertion tube while retaining the orthopedic implant in the interspinous space.

2. A method as in claim 1, wherein distraction of the spinous processes of the first and second vertebral bones is performed during the implantation method in a manner comprising:
   advancing a first segment of a threaded first distraction screw into a bony surface of the spinous process of the first vertebral bone, wherein the first distraction screw is advanced into the spinous process of the first vertebral bone in a direction of a long axis of the spinous process, wherein the first distraction screw has a second segment that couples to a distraction platform and wherein the distraction platform can deliver a distractive force through the first distraction screw to the spinous process of the first vertebral bone;
   coupling a first segment of a second distraction screw onto a segment of the second vertebral bone, wherein the second distraction screw has a second segment that couples to the distraction platform and wherein the distraction platform can deliver a distractive force through the second distraction screw to the second vertebral bone;
   actuating the distraction platform in order to displace the spinous process of the first vertebral bone relative to the spinous process of the second vertebral bone; and
   removing at least one threaded distraction screw while retaining the positioned orthopedic implant.

3. A method as in claim 1, wherein the method is performed under radiographic guidance.

4. A method as in claim 1, wherein the method is performed as a minimally invasive procedure.

5. A method as in claim 1, wherein the method is performed as a percutaneous procedure.

6. A method as in claim 1, wherein the orthopedic implant is advanced in a straight trajectory into the target interspinous space.

7. A method as in claim 1, wherein a trajectory of the orthopedic implant parallels the plane of the vertebral midline.

8. A method for placement of an orthopedic implant into a target interspinous space that is between spinous processes of a first vertebral bone and a second immediately adjacent vertebral bone of a subject, comprising:
   providing an implant insertion tube having an elongated body and extending along a first straight axis from a proximal aperture to a distal aperture, wherein an internal bore of the elongated body is sized and shaped to permit passage of the orthopedic implant from the proximal aperture to the distal aperture;
   positioning the implant insertion tube posterior to the target interspinous space and on one side of a vertebral midline, wherein the vertebral midline is defined by a mid-sagittal plane that is used to divide a vertebral bone into right and left halves, and wherein the first axis of the implant insertion tube is aligned parallel to the mid-sagittal plane;
   advancing the orthopedic implant through the internal bore of the implant insertion tube and into the target interspinous space, wherein the orthopedic implant is advanced in a curvilinear trajectory as it traverses the internal bore; and
   removing the insertion tube while retaining the orthopedic implant in the interspinous space.

9. A method as in claim 8, wherein distraction of the spinous processes of the first and second vertebral bones is performed during the implantation method in a manner comprising:
   advancing a first segment of a threaded first distraction screw into a bony surface of the spinous process of the first vertebral bone, wherein the first distraction screw is advanced into the spinous process of the first vertebral bone in a direction of a long axis of the spinous process, wherein the first distraction screw has a second segment that couples to a distraction platform and wherein the distraction platform can deliver a distractive force through the first distraction screw to the spinous process of the first vertebral bone;

coupling a first segment of a second distraction screw onto a segment of the second vertebral bone, wherein the second distraction screw has a second segment that couples to the distraction platform and wherein the distraction platform can deliver a distractive force through the second distraction screw to the second vertebral bone;

actuating the distraction platform in order to displace the spinous process of the first vertebral bone relative to the spinous process of the second vertebral bone; and removing at least one threaded distraction screw while retaining the positioned orthopedic implant.

10. A method as in claim 8, wherein the distal aperture forms an opening within a side wall of the elongated body.

11. A method as in claim 8, wherein the method is performed under radiographic guidance.

12. A method as in claim 8, wherein the method is performed as a minimally invasive procedure.

13. A method as in claim 8, wherein the method is performed as a percutaneous procedure.

14. A method for the placement of an orthopedic implant into a target interspinous space that is between spinous processes of a first and a second immediately adjacent vertebral bones, comprising:

providing an implant insertion assembly having a member with an elongated body that extends along a first axis from a proximal aperture to a distal aperture, wherein the elongated body has an internal bore that connects the proximal and distal apertures, wherein at least a segment of the internal bore extends along the first axis in a curvilinear trajectory, and wherein a proximal aspect of the elongated body is coupled to a platform that is adapted to limit movement of the elongated body relative to the target interspinous space;

positioning the implant insertion assembly posterior to the target interspinous space, wherein the distal aperture of the elongated body is positioned in proximity to the target interspinous space; and advancing the orthopedic implant through the internal bore of the elongated body and into the target interspinous space.

15. A method as in claim 14, wherein the method is performed under radiographic guidance.

16. A method as in claim 14, wherein the method is performed as a minimally invasive procedure.

17. A method as in claim 14, wherein the method is performed as a percutaneous procedure.

* * * * *